United States Patent [19]

Frehel et al.

[11] Patent Number: 4,500,534
[45] Date of Patent: Feb. 19, 1985

[54] THIENO-PYRIDINONE DERIVATIVES, PROCESS FOR ITS PREPARATION, AND ANTI-BLOOD-PLATELET AND ANTI-THROMBOTIC APPLICATIONS THEREOF

[75] Inventors: Daniel Frehel, Toulouse; Jean-Pierre Maffrand, Portet; Eric Vallee, Tournefeuille, all of France

[73] Assignee: Sanofi, S.A., Toulouse, France

[21] Appl. No.: 504,524

[22] Filed: Jun. 15, 1983

[30] Foreign Application Priority Data

Jun. 16, 1982 [FR] France .................................. 82 10926

[51] Int. Cl.³ .................... A61K 31/435; C07D 495/04
[52] U.S. Cl. ....................................... 514/301; 546/114
[58] Field of Search .......................... 546/114; 424/256

[56] References Cited

U.S. PATENT DOCUMENTS 4,424,356 1/1984 Maffrand et al. .................... 546/114

Primary Examiner—Henry R. Jiles
Assistant Examiner—Bernard I. Dentz
Attorney, Agent, or Firm—Weiser & Stapler

[57] ABSTRACT

This invention relates to a new thieno-pyridinone derivative of the formula:

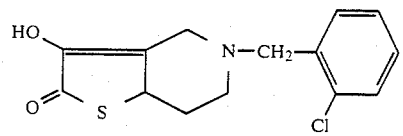

and its pharmaceutically acceptable inorganic or organic acid addition salts.

This invention relates also to a process for the preparation of said compound and to its therapeutic application as blood-platelet anti-aggregation agent and anti-thrombosis agent.

8 Claims, No Drawings

THIENO-PYRIDINONE DERIVATIVES, PROCESS FOR ITS PREPARATION, AND ANTI-BLOOD-PLATELET AND ANTI-THROMBOTIC APPLICATIONS THEREOF

The present invention relates to a new 5,6,7,7a-tetrahydro-4H-thieno(3,2-c)pyridin-2-one derivative, to a process for its preparation, and to its applications in human and veterinary medicine.

The compound of this invention has the following formula (I):

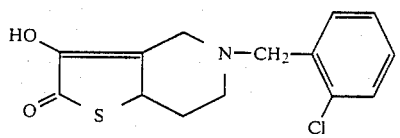

and its pharmaceutically acceptable inorganic or organic acid addition salts are also included in the invention.

Due to the presence of an asymmetrical carbon atom, this compound may exist in two enantiomeric forms. Thus, this invention concerns both the individual enantiomers and their mixture.

This invention relates also to a process for the preparation of the compound of the formula (I) according to the invention, comprising:

(a) nitrosating a compound of the formula (II):

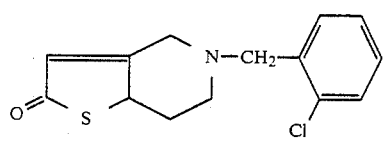

(b) hydrogenating the resulting keto-oxime of the formula (III):

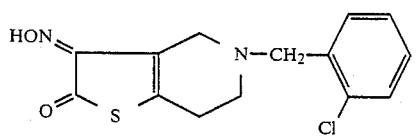

(c) submitting the resulting hydrogenated compound, of the formula (IV)

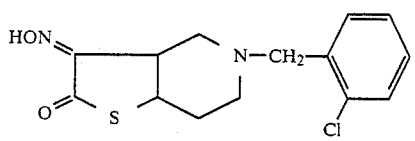

to an acid treatment, to give the desired derivative of the formula (I).

The compound of the formula (II), which is the starting material for the preparation of the compound of this invention, is described (together with the process for its preparation) in French patent application No. 80 25 274 filed by Applicant.

The nitrosation step which provides the compound of the formula (III), i.e., 5-(2-chloro-benzyl)-3-(hydroxyimino)-4,5,6,7-tetrahydro-3H-thieno(3,2-c)pyridin-2-one, is effected in glacial acetic acid medium under an inert atmosphere, by reacting the compound of the formula (II) with sodium nitrite.

The hydrogenation step is carried out in the presence of perchloric acid and a catalyst, preferably palladium-on-charcoal dissolved in an alcohol such as methanol, ethanol, isopropanol, or in an aqueous-alcoholic solvent, at a temperature from 10° C. to 50° C.

The acid treatment is effected on the compound of the formula (IV), dissolved in a mixture consisting of an alcohol such as methanol, ethanol or isopropanol, and of an acid such as hydrochloric or hydrobromic acid at concentrations from 1N to 3N. This step is effected under refluxing conditions, under an inert atmosphere, and for a period of time from 3 hours to 6 hours.

The following non-limiting Examples illustrate the present invention.

(a) 5-(2-Chloro)-3-(hydroxyimino)-4,5,6,7-tetrahydro-3H-thieno(3,2-c)pyridin-2-one 5-(2-Chloro-benzyl)-5,6,7,7a-tetrahydro-4H-thieno-(3,2-c)-pyridin-2-one oxalate (25 g; 0.0068 mole) is suspended in glacial acetic acid (125 ml), under an inert atmosphere, and, after cooling the reaction medium to 0°–5° C., sodium nitrite (5 g; 0.072 mole) dissolved in water (30 ml) is added dropwise thereto. The resulting material is left at room temperature for 7 hours. The crystals are filtered off, washed with ether and dried. The product is recrystallised from water, to give yellow crystals; M.p.=222° C.; Yield: 70%.

(b) 5-(2-Chloro-benzyl)-3-(hydroxyimino)-3a,4,5,6,7,7a-hexahydro-3H-thieno(3,2-c)-pyridin-2-one The previously obtained compound of the formula (III) (15 g; 0.0376 mole) is dissolved in a mixture of methanol (900 ml) and 70% perchloric acid (8 ml). 4 g of 10% Palladium-on-charcoal suspended in ethanol (100 ml) are added to the reaction medium. The reaction medium is hydrogenated in a reactor under ordinary pressure (1 atm.) and is then left at room temperature for 6 hours. After filtering off the catalyst, the reaction medium is evaporated to dryness.

The resulting residue is dissolved in water and is then neutralised with a saturated aqueous sodium bicarbonate solution. The aqueous phase is extracted with dichloromethane, the organic phase is dried over anhydrous sodium sulfate and is then evaporated to dryness. The oily residue is purified by column chromatography over silica (eluent: toluene-ethyl acetate 1:1).

Final purification is effected via the oxalate. Beige crystals, M.p.=200° C.; Yield: 65%.

(c) 5-(2-Chloro-benzyl)-3-hydroxy-5,6,7,7a-tetrahydro-4H-thieno(3,2-c)-pyridin-2-one The compound of the formula (IV) (10.4 g; 0.0334 mole) obtained in the preceding step is dissolved in a mixture of isopropyl alcohol (250 ml) and 2N hydrochloric acid (45 ml). The resulting solution is refluxed for 4 hours under an inert atmosphere. It is then evaporayed to dryness and the residue is taken up into a saturated aqueous sodium bicarbonate solution. The aqueous phase is extracted with dichloromethane. The organic phase is dried over anhydrous sodium sulfate and evaporated to dryness. The resulting oily residue is purified by filtration through a silica bed (eluent: toluene-ethyl acetate 1:1). The base is obtained in a yield of 81%, as beige crystals, M.p.=121° C.

Different salts were prepared according to conventional methods:

hemioxalate: cream coloured crystals, M.p.=170° C. (recrystallisation from isopropyl alcohol-acetonitrile), nitrate: pink crystals, M.p.=181° C. (recrystallisation from isopropanol-methanol), hydrochloride: beige crystals, M.p.=139° C. (recrystallisation from isopropanol).

This invention relates also to a therapeutic composition having in particular an anti-blood platelet aggregation and an anti-thrombosis activity, comprising, as active ingredient, a derivative of the formula (I) or a pharmaceutically acceptable inorganic or organic acid addition salt thereof.

The toxicological investigation concerned the acute, chronic, sub-chronic and delayed toxicities and provided evidence of the good tolerance and low toxicity of the derivative of this invention.

The tests carried out in mice, rats and rabbits show that the administration (whether orally or intraperitoneally) of the derivative of this invention never caused any local or systemic reaction, any perturbation in the regularly effected biological controls, and any macroscopic or microscopic lesion throughout the different tests carried out.

The pharmacological investigation provided evidence of the anti-blood-platelet aggregation and anti-thrombosis actions of the compound of this invention.

1—ANTI-BLOOD-PLATELET AGGREGATION ACTION

The experimentation was conducted in rats which were administered orally 100 mg of the compound of this invention, for 3 days, at times −48 hrs, −24 hrs and −2 hrs. At time 0, a 4 ml sample of blood was taken from the jugular vein of the anesthesized animal, according to Renaud's technique. It is this citrated blood which is used in the aggregation determinations.

(a) Determination of A.D.P.-induced blood-platelet aggregation 2 ml citrated blood are rapidly poured into a small beaker placed in a magnetic stirrer provided with a magnet bar. After stirring for a few seconds, 0.4 ml of a solution containing 0.66 µg adenosine-diphosphate (A.D.P.) per ml is introduced in the beaker. After stirring for 5 seconds, two 0.5 ml blood samples are taken:

the first sample is mixed with 0.5 ml of an EDTA-formaldehyde solution, the second sample is mixed with only 0.5 ml of an EDTA solution.

The purpose of the EDTA-formaldehyde addition is to stabilise the blood and thus, to fix the aggregation, while, in contrast, EDTA causes the de-aggregation of all the blood-platelet aggregates.

Both mixtures are left aside for 10 minutes and are then submitted to a low-speed centrifugation for 5 minutes, to separate the red corpuscles, after which the supernatant platelet-rich plasma (PRP) is removed, diluted and submitted to a platelet count.

The aggregation level is determined according to the ratio:

$$\frac{\text{number of platelets in EDTA-formaldehyde}}{\text{number of platelets in EDTA}} \times$$

100 = percent unaggregated platelets

The closer the ratio is to 100, the higher the inhibiting effect of the test material on blood-platelet aggregation.

It was thus determined that in the group (5 rats) treated with the compound of this invention, the percentage obtained is 44±13, whereas in the control group (5 rats) the percentage is 6±2.

(b) Determination of collagen-induced blood-platelet aggregation

To 0.5 ml citrated blood is added 0.10 ml of a solution containing 10 µg collagen par ml. The blood-platelet count is effected uninterruptedly, while maintaining the medium under constant stirring.

The decrease of the number of free blood-platelets as a function of time is followed continuously and permits drawing a curve the slope of which gives the initial speed of aggregation.

For the group treated (5 rats) with the compound of this invention, the initial aggregation speed is 2.33+1.18, while for the untreated group (5 rats) it is 12.44+2.65.

The study of the inhibiting activity on blood-platelet aggregation related also to the action of the compound of this invention with respect to bleeding time.

The method used is an adaptation of the technique according to L. STELLA, M. B. DONATI & G. de GAETANO, Thromb. Res., 1975, 7, 709–716.

The experiment is carried out in rats which were orally treated 65 hrs, 41 hrs and 17 hrs previously, with 200 mg of the compound of this invention suspended in 10 ml/kg of a 5% aqueous gum arabic solution. After pentobarbital anesthesia, the tail is cut 5 mm from its end. The blood is carefully dabbed off at 15 second intervals, care being taken not to touch the wound.

Hemostasis is attained when bleeding ceases for one minute.

Bleeding times are expressed in seconds and times in excess of 1,200 seconds (20 minutes) are not counted any further.

It was thus determined that in the controls administered only gum arabic the average bleeding time is 390 seconds, while it is in excess of 1,200 seconds in the case of the treated animals.

2—ANTI-THROMBOSIS ACTIVITY

This activity was investigated according to 2 methods.

(a) Experimental thrombosis method, on silk thread

The principle of this study is an adaptation of the experimental thrombosis method by extra-corporeal circulation, described by TERUHIKO UMETSU & KAZUKO SANAI (THROMB. HAEMOST., 39, 1, 1978).

The left jugular vein and the right external carotid artery of a rat anesthesized with an intraperitoneal pentobarbital injection are bared.

The arterial-venous shunt consists of a central catheter and two lateral catheters; a white natural silk thread is introduced into the central portion and the blood flow is re-established for 20 minutes. After interruption of the blood flow by clamping, the thread is gently removed and is immediately weighed. The average weight of a damp silk thread had been determined previously.

Treatment is carried out 48 hrs, 24 hrs and 2 hrs before the beginning of the blood flow through the shunt, by oral administration of 200 mg/kg of the compound of this invention suspended in 10 ml/kg of a 5% gum arabic solution, the control being administered only the 5% gum arabic solution.

It was thus determined that the average thrombus weight in both groups of 10 rats was 38.62±1.18 mg for the control animals and 25.00±6.42 mg for the treated animals (−35 percent), respectively.

(b) Venous thrombosis method, using a metal helix

This method is an adaptation of the method according to FRIEDMAN & co-workers (AM. J. PHYSIOL., 1960, 199, 770-774). A metal helix (a paste filling device used by dentists) is cut down to size and inserted in the lower vena cava of rats which have been administered 48 hrs, 24 hrs and 2 hrs previously an oral treatment of 200 mg/kg of the test compound suspended in 10 ml/kg of a 5% aqueous gum arabic solution.

Five hours later, this metal helix is removed together with the thrombus it retains, is delicately dried by successive dabbing with filter paper, and weighed. The thrombus is then removed from the metal helix which is again dried and weighed. The average thrombus weight is thus obtained by difference: it is 3.4±0.4 mg for the reference rats (10 rats) who were administered only gum arabic, and 2.1±0.3 mg for the rats (10 animals) treated with the active ingredient of this invention (−36%).

The toxicological and pharmacological investigations reported above provide evidence of the low toxicity of the compound of this invention and of its excellent tolerance together with its interesting anti-blood-platelet aggregation and anti-thrombosis properties which make them most valuable for therapeutic purposes in human and veterinary medicine.

The therapeutic composition of this invention may be formulated for oral administration as tablets, coated tablets, capsules, drops, granules or syrup. It may also be formulated for rectal administration as suppositories and, for parenteral administration, as injectable solutions.

Each dosage unit contains advantageously 0.010 g to 0.500 g of the compound of this invention, the daily dosage regimen varying from 0.025 g to 1.50 g active ingredient depending on the age of the patient and on the severity of the condition treated.

Non-limiting Examples of pharmaceutical formulations of the active ingredient of this invention are given below.

| 1/ Tablets | |
|---|---|
| Active ingredient | 0.15 g |
| Excipients: lactose, starch, gum arabic, magnesium stearate | |
| 2/ Coated tablets | |
| Active ingredient | 0.100 g |
| Excipients: polyvidone-excipient, gelatin, stearic acid, corn starch, lactose, white sugar, gum arabic, tartrazine, new coccine | |
| 3/ Capsules | |
| Active ingredient | 0.250 g |
| Excipients: corn starch, magnesium stearate, anhydrous calcium sulfate. | |
| 4/ Injectable solution | |
| Active ingredient | 0.100 g |
| Isotonic solvent | to make 5 ml |
| 5/ Suppositories | |
| Active ingredient | 0.150 g |
| Excipient: semi-synthetic triglycerides | |

In view of its anti-blood-platelet aggregation and anti-thrombosis properties, the compound of this invention is applicable in the prevention and the treatment of diseases inducing a pathological modification of blood-platelet aggregation, such as thrombo-embolic diseases.

We claim:

1. 5,6,7,7a-Tetrahydro-4H-thieno(3,2-c)pyridin-2-one derivative, having the following structural formula (I):

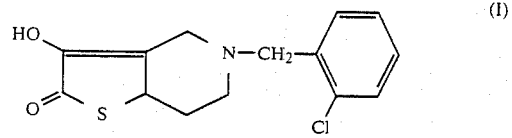

and its pharmaceutically acceptable inorganic or organic acid addition salts.

2. Process for the preparation of the compound of the formula (I) as claimed in claim 1, comprising:

(a) nitrosating a compound of the formula (II):

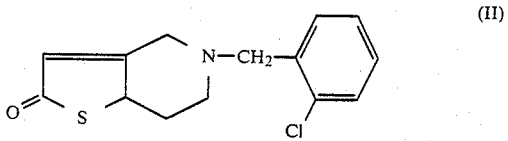

(b) hydrogenating the resulting keto-oxime, of the following formula (III):

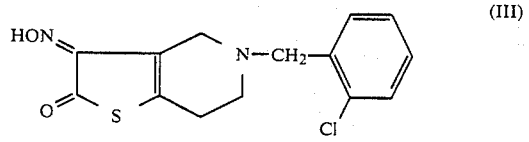

(c) submitting the resulting hydrogenated derivative, of the following formula (IV):

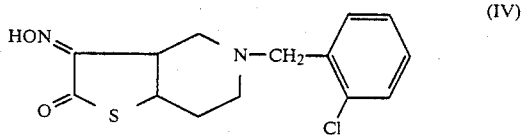

to an acid treatment, to give the desired derivative of the formula (I).

3. Process as claimed in claim 2, wherein the nitrosation is effected with sodium nitrite in glacial acetic acid medium and under an inert atmosphere.

4. Process as claimed in claim 3, wherein the hydrogenation is effected in the presence of a catalyst and of perchloric acid.

5. Process as claimed in claim 3, wherein the acid treatment is preferably effected with hydrochloric acid at 2N concentration, under refluxing conditions and under an inert atmosphere.

6. Therapeutic composition having in particular anti-blood-platelet aggregation and anti-thrombosis activities, said composition comprising, an effective amount of the derivative as claimed in claim 1 and a suitable pharmaceutical carrier.

7. Therapeutic composition as claimed in claim 6, formulated in a form suitable for oral, parenteral or rectal administration.

8. Therapeutic composition as claimed in any one of claims 6 and 7, in dosage unit form, each unit dose containing from 0.010 g to 0.500 g active ingredient.

* * * * *